United States Patent [19]

MacKeen et al.

[11] Patent Number: 4,915,684

[45] Date of Patent: Apr. 10, 1990

[54] METHOD AND APPARATUS FOR MODULATING THE FLOW OF LACRIMAL FLUID THROUGH A PUNCTUM AND ASSOCIATED CANALICULUS

[76] Inventors: Donald L. MacKeen, P.O. Box 40813, Washington, D.C. 20016; Hans-Walter Roth, 73 Im Grund, D-79-VLM-10, Fed. Rep. of Germany

[21] Appl. No.: 209,601

[22] Filed: Jun. 21, 1988

[51] Int. Cl.⁴ .......................................... A61M 27/00
[52] U.S. Cl. ........................................ 604/8; 604/264; 604/294
[58] Field of Search ........................... 604/8–10, 604/54, 264, 294; 128/341, 343

[56] References Cited

U.S. PATENT DOCUMENTS

| | | | |
|---|---|---|---|
| 2,154,968 | 4/1939 | Alkio | 604/264 X |
| 3,726,284 | 4/1973 | Parker | 604/8 |
| 3,948,272 | 4/1976 | Guibor | 604/264 |
| 3,949,750 | 4/1976 | Freeman | 128/341 X |
| 4,305,395 | 12/1981 | Martinez | 604/54 X |
| 4,380,239 | 4/1983 | Crawford | 604/28 |
| 4,660,546 | 4/1987 | Herrick | 128/1 R |
| 4,747,818 | 5/1988 | Edelschick | 604/8 |
| 4,787,885 | 11/1988 | Binder | 604/8 |

*Primary Examiner*—Dalton L. Truluck
*Attorney, Agent, or Firm*—Bradford E. Kile

[57] ABSTRACT

A lacrimal fluid modulating device for controlling the flow of lacrimal fluid through a punctum and associated canaliculus of a human eye comprising a generally cylindrical body member with an axial bore, an arcuate head member and peripheral placement and retaining members fashioned upon an exterior surface of the cylindrical body.

12 Claims, 2 Drawing Sheets

METHOD AND APPARATUS FOR MODULATING THE FLOW OF LACRIMAL FLUID THROUGH A PUNCTUM AND ASSOCIATED CANALICULUS

RELATED PATENT

This application is related to the subject matter of prior U.S. Pat. No. 3,949,750 entitled "Punctum Plug Method for Treating Keratoconjunctivitis Sicca (Dry Eye) and Other Ophthalmic Ailments Using Same" issued Apr. 3, 1976.

BACKGROUND OF THE INVENTION

This invention relates to a method and apparatus for the treatment of tear-related disorders. More specifically, this invention relates to a method and apparatus which is used to treat cases of mild to moderate keratitis sicca or keratoconjunctivitis sicca (dry eye) conditions and contact lens wearing problems as well as pathologically dilated or constricted punctae.

Dry eye describes a continuum of problems which range from discomfort, to decreased vision and pain, to blindness. Its causes are aging, disease inflammatory processes and prescription drug side effects. A common condition is an inability to maintain a stable preocular tear film (PTF).

A film of tears, spread by the upper eyelid over the corneal and conjunctival epithelia, makes the surface of the eye smooth and optically clear. The tear film is composed of three thin layers which coat the surface of the eye. An outermost layer, an oily layer, is produced by small glands called meibomian glands at the edge of the eyelid. This outermost layer provides a smooth tear surface and reduces evaporation of tears. A middle watery layer is produced by the large lacrimal gland and a plurality of small glands scattered throughout the conjunctiva. This watery layer produces the largest amount of fluid and cleanses the eye by washing away foreign particles and irritants. An innermost layer consists of mucus produced by goblet cells in the conjunctiva. This inner layer allows the watery layer to spread evenly over the surface of the eye and helps the eye to remain wet. The mucus produced by this innermost layer adheres tears to the eye.

Normally the PTF is formed by a cooperative interaction of products from the meibomian glands, the lacrimal glands, and goblet cells; however, dry eye results when these glands produce less than an adequate amount of tears.

The treatment of dry eye is a common phenomenon. Tear deficiencies cause chronic irritation of the anterior segment, resulting in complaints of sandy, itching eye, conjunctivitis, metabolic disturbances of the cornea, and in extreme cases, a loss of visual function. Patients often present complaints and problems associated with a partial decrease in aqueous tear production. One cause of such complaints is partial atrophy of the lacrimal glands which is seen often in an aged patient and in some patients following infection. Atrophy can also occur in a younger patient wearing high water-content contact lenses, because of the increased requirement of the anterior segment for aqueous tears.

Thermal occlusion of the punctae opening and/or the proximal canaliculus has been employed in the treatment of dry eye conditions in the past. Initially performed with cautery or diathermy, permanent occlusion is now performed with the aid of medical grade lasers. When PTF loss into the naso-lacrimal trap is blocked, the volume of the remaining tears provide enhanced wetness of the anterior segment.

Epiphora and occasionally infections are two disadvantages of permanent occlusion. Also, there is a destruction of normal tissue which requires surgical intervention to reverse.

In order to avoid one or more of the foregoing disadvantages, alternative methods of temporary occlusion of a punctal opening have been developed. Such methods include temporary occlusion of the canaliculus by the insertion of small rods made from gelatin or collagen, or the use of temporary plugs made from bone cement. The blocking action of these agents is often either too brief or otherwise unsatisfactory.

As an alternative, patients with minor tear deficiencies were forced to use chronic multiple daily treatments with eye drops or cellulose inserts. Those with contact lens problems occasion decreased daily wear times or abandoned lens wear entirely.

The foregoing noted problems of mild to moderate dry eye were advantageously addressed by the introduction of a punctum plug as disclosed and claimed in the previously identified Freeman U.S. Pat. No. 3,949,750. The disclosure of this patent, of common assignment with the subject application, is incorporated herein by reference as though set forth at length.

Total occlusion of a lower punctum with a silicone plug of the Freeman design has proved beneficial in a number of patients suffering from moderate dry eye conditions.

Although reversible, this method of total occlusion is inappropriate for a very young person with very mild symptoms or with many problems associated with high water content contact lenses where it may be advantageous to diminish but not stop an outflow of lacrimal fluid.

The problems suggested in the preceding are not intended to be exhaustive, but rather are among many which may tend to reduce the effectiveness of prior methods and apparatus for modulating the flow of lacrimal fluid through a punctum and associated canaliculus. Other noteworthy problems may also exist; however, those presented above should be sufficient to demonstrate that methods and apparatus for treating the moderate loss of PTF appearing in the past will admit to worthwhile improvement.

OBJECTS AND SUMMARY OF THE INVENTION

Objects

It is therefore a general object of the invention to provide a novel method and apparatus which will obviate or minimize problems of the type previously described.

It is another object of the invention to provide a method and apparatus to alleviate symptoms of moderate PTF loss without occluding the punctum of a patient's eye.

It is yet another object of the invention to enhance the retention of PTF for patients having pathologically dilated or constricted punctae.

It is still another object of the invention to provide a novel method and apparatus to alleviate the symptomology of medium to moderate dry eye by modulating the flow of lacrimal fluid or PTF that is permitted to flow away from a patient's eye.

It is a further object of the invention to provide a novel method and apparatus to alleviate the symptoms of dry eye for wearers of high water content contact lenses.

It is yet a further object of the invention to provide a method and apparatus for modulating the flow of lacrimal fluid from a patient's eye without surgically occluding a punctum opening.

It is yet still another object of the invention to provide a method and apparatus for modulating the flow of lacrimal fluid away from a patient's eye with an easily reversible procedure.

It is another object of the invention to provide a novel method and apparatus for modulating lacrimal flow of fluid away from a patient's eye a predictable constant degree.

BRIEF SUMMARY OF THE INVENTION

One preferred embodiment of the invention which is intended to accomplish at least some of the foregoing objects comprises a lacrimal fluid modulating device composed of a generally cylindrical body portion with an enlarged cap at one, inlet, end and a tapered peripheral enlargement at an outlet end. An axial bore extends completely through the modulating device and is fashioned with an outlet end having an internal diameter which is preferably no less than 0.12 mm and no greater than 0.36 mm.

In one embodiment the enlargement at the outlet end comprises a double inclined ramp operable to facilitate insertion of the modulating device into a punctal opening and associated canaliculus of a patient. Once inserted the peripheral enlargements maintain the device in an operative secure position.

In one embodiment of the invention, the axial bore may be tapered from an inlet end to a smaller diameter outlet end. In a further embodiment of the invention, the axial bore may be stepped from a first axial bore at an inlet end of the modulating device to a smaller axial bore at an outlet end of the device.

THE DRAWINGS

Other objects and advantages of the present invention will become apparent from the following detailed description of preferred embodiments taken in conjunction with the accompanying drawings wherein.

Figure 3:
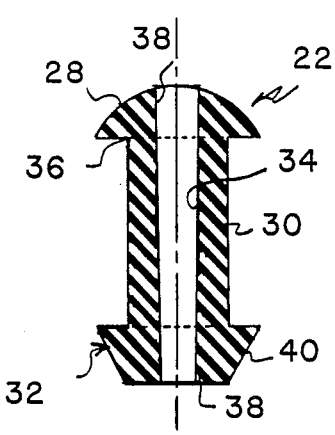
Figure 4:
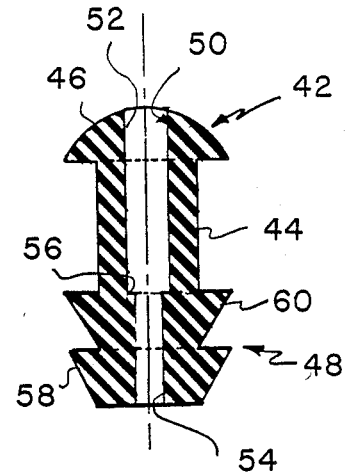

FIG. 3 a detailed cross-sectional view of a lacrimal fluid modulating device in accordance with one embodiment of the invention including an axial bore;

FIG. 4 is a detailed cross-sectional view, similar to FIG. 3, of a lacrimal fluid modulating device in accordance with another preferred embodiment of the invention including a stepped axial bore and a plurality of enlarged retaining members at an outlet end of the device; and FIGS. 5A-5F disclose a sequence of installation of a lacrimal fluid modulating device in accordance with the subject invention.

DETAILED DESCRIPTION

Context of the Invention

Figure 1:
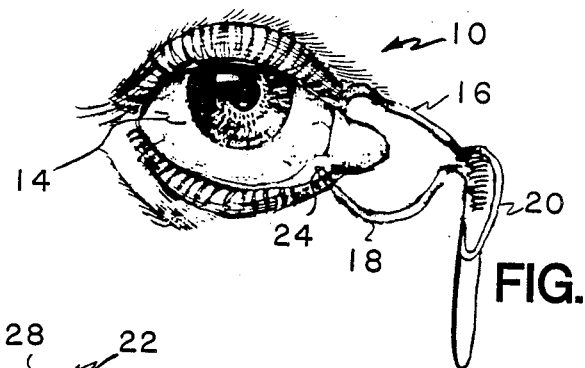
FIG. 1 is an axonometric view, partially broken away, disclosing the anatomy of a human eye including attached upper and lower lacrimal ducts or canaliculus which operably connect to lacrimal sac and ultimately a nasal passage.

Before discussing in detail a method and apparatus for modulating the flow of lacrimal or PTF fluid away from a human eye surface, it may be useful to briefly discuss the context of the invention in association with FIG. 1. More specifically the anatomy of an eye is illustrated including an outer corneal surface 14 which is lubricated by a thin PTF which coats the surface of the eye. This thin film is composed of three layers: an outer oily layer, intermediate watery layer and an innermost layer of mucus.

The outermost layer of tear film is produced by meibomian glands at the edge of the eyelid. The primary purpose of this oily layer is to smooth the tear surface and reduce evaporation of tears. The middle layer, and largest of the three, makes up most of what one ordinarily considers tears. This watery layer is produced by small glands scattered throughout the conjunctiva, which is the delicate membrane lining the inside of the eyelid and covering the eyeball, and by a major tear gland called the large lacrimal gland. This layer cleanses the eye and washes away foreign particles or irritants. The innermost layer consists of mucus produced by other cells in the conjunctiva. This layer allows the watery layer to spread evenly over the surface of the eye and helps the eye to remain wet. Without mucus, tears would not adhere adequately to the eye surface.

Maintaining PTF over the eye, by blinking, makes the surface of the eye smooth and optically clear. Without the PTF as noted above, good vision would not be possible. In instances where tear film is not adequate, a patient may encounter symptoms of stinging, burning, scratchiness, stringy mucus and excess irritation from smoke. Moreover, problems with high water content, contact lenses may cause symptoms of dry eye, or where a patient has an inadequate flow of lacrimal fluid may make it impossible to wear contact lenses. In addition some prescription drugs may produce symptoms of PTF deficiency.

Tears which lubricate the eye are produced around the clock and excessive tearing is drained away from the eye surface through an upper 16 and lower 18 lacrimal duct better known as the canaliculus, and into a lacrimal sack 20 and ultimately into the nasal cavity.

Lacrimal Fluid Modulating Device

Figure 2:
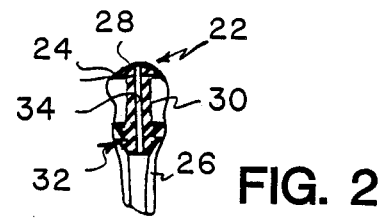
FIG. 2 is a detailed cross sectional view of a punctum and associated canaliculus of a human eye, such as illustrated in FIG. 1 with a lacrimal fluid modulating device positioned in accordance with one preferred embodiment of the invention.

In certain instances, such as discussed in the preceding, it may be desirable to modulate the flow of lacrimal fluid escaping away from an eye surface. This may be accomplished in accordance with a preferred embodiment of the invention by the provision of a lacrimal fluid modulating device 22 such as illustrated in FIG. 2. More specifically, the lacrimal fluid modulating device is inserted through an annular punctal opening 24, note also FIG. 1, and into an associated canaliculus 26.

The lacrimal fluid modulating device includes a head portion 28 at a first inlet, end of the device, a generally cylindrical body portion 30 and an enlarged tip portion 32 at a second outlet, end of the unit. An axial bore 34 extends through the lacrimal fluid modulating device 22 and serves to meter the passage of lacrimal fluid through the punctal opening and through its associated canaliculus.

Referring now specifically to FIG. 3, there will be seen a detailed cross-sectional view of a lacrimal fluid modulating device 22 in accordance with one preferred embodiment of the invention. A generally cylindrical body member 30 includes a first, inlet, end 36 and a second, outlet, end 38. An arcuate head member 28 is fashioned at the first end 36 of the generally cylindrical body 30 and includes a bore 38 which is coaxial with a bore 34 extending axially through the body member. An exterior diameter of the rounded head member is greater than the exterior diameter of the generally cylindrical body member 30 and operably serves to rest upon a punctal opening 24 to prevent the lacrimal fluid modulating device from falling into an associated canaliculus 26.

A peripheral member 32 is fashioned about an exterior surface of the generally cylindrical body member at the second end of the body member. This peripheral member may be advantageously fashioned with a conical outer surface 40 which extends upwardly and outwardly from the distal end 38 of the body member for facilitating placement of the modulating device through a punctal opening of a patient and synergistically for retaining said cylindrical body member within an associated canaliculus; note again FIG. 2.

The axial bore 34 extends completely through the generally cylindrical body member and operates in cooperation with the bore 38 through the cap to modulate the flow of lacrimal fluid away from the surface of an eye, through the punctum and associated canaliculus. This controlled bore diameter may be advantageously utilized to enhance the retention of lacrimal fluid or PTF within the eye of a patient. In certain instances of dry eye an enlarged punctal opening may permit lacrimal fluid to flow away from the eye surface too freely. In other instances a reduced production of tear film may result in a dry condition of an eye even when the punctal opening and associated canaliculus are anatomically normal. In either instance, insertion of a lacrimal fluid modulating device, in a manner depicted in FIG. 2, will provide a degree of predictability with respect to the diameter of the passage and thus the rate of flow of fluid away from a patient's eye and into an associated canaliculus.

The bore 34 may have a uniform diameter throughout or in certain instances may be advantageously tapered from the inlet end to the outlet end. At the outlet end 38, the bore may be reduced to a optimum desired diameter for the condition of dryness experienced by a particular patient. It has been found that the optimum range for this outlet diameter is not less than 0.12 mm and not greater than 0.36 mm in diameter with an optimum diameter being 0.24 mm.

In addition to the insertion and retaining functions provided by the enlarged peripheral surface 32, the structural integrity of the designed operative diameter of the outlet end of the modulating device 22 is advantageously maintained by the enlarged cross sectional area at the outermost or distal end of the lacrimal fluid modulating device.

Turning to FIG. 4, there will be seen an alternate preferred embodiment of the invention comprising a lacrimal fluid modulating device including a cylindrical body portion 42, an arcuate head portion 44 integrally joined at a first, inlet, end of the lacrimal fluid modulating device and a peripheral means 48 positioned about a second, outlet, end of the device 42. An axial bore 50 is fashioned through the modulating device 42 and includes a first inlet diameter 52 and a second smaller outlet diameter 54 which is stepped with respect with the initial inlet diameter 52. The outlet diameter 54 is peripherally not less than 0.12 mm and not greater than 0.36 mm in diameter and in a preferred embodiment is 0.24 mm.

As previously mentioned, the outlet bore 54 has a internal diameter less than that of inlet bore 52 and thereby forms an internal ledge 56 within the cylindrical body 44. This ledge advantageously cooperates with the distal end of an inserting tool in a manner which will be discussed in detail herein below.

The peripheral means 48 fashioned about the exterior surface of the generally cylindrical body is composed of a first 58 and second 60 conical portion which extends upwardly and outwardly to form in combination a plurality of reinforcing and retaining rings. More particularly, the sloped wall surfaces of the first conical member 58 operably functions to facilitate insertion of the lacrimal modulating device through a patient's punctae and into an associated canaliculus. Once inserted the plurality of peripheral rims 58 and 60 operably interact with an interior wall surface of the associated canaliculus, note FIG. 2, to operably secure the lacrimal fluid modulating device in a secure axial position. In addition, the peripheral members 58 and 60 serve to reinforce and stabilize the internal dimensional characteristics of the outlet end of the lacrimal fluid modulating device and maintain the outlet bore in an open condition.

The previously noted lacrimal fluid modulating devices may be formed from a plurality of biologically inert materials such as polytetrafluorethylene (Teflon), hydroxyethylmethacrylate (HEMA), polymethylmethacrylate, (PMMA) and various compositions of medical grade silicon, etc.

Method of Installation

Referring now to FIGS. 5A–5F, there will be seen a sequence of views suitable for use in inserting a lacrimal fluid modulating device into the puncta and associated canaliculus of a patient.

Figure 5A:
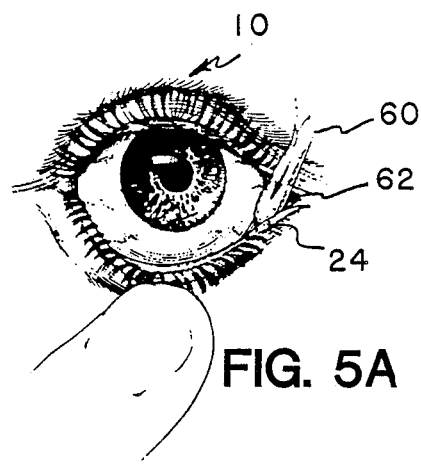
Figure 5B:
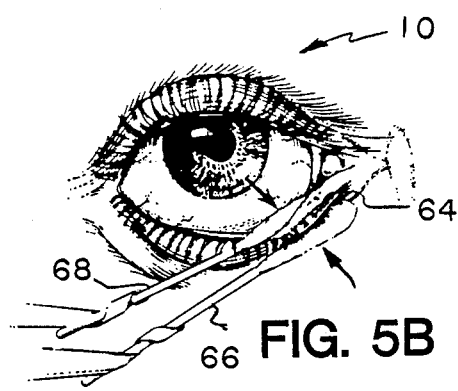

More specifically and with reference to FIG. 5A, prior to insertion, the area of the punctal opening 24, of a patient's eye 10, may be anesthetized with a topical anesthetic such as lidocaine through application with a cotton tip applicator 60. Alternatively, proparachine HCl (e.g., Opthaine, Opthetic) may be inserted into the area 62 of a patient's eye adjacent to the punctal opening 24.

A modulating device is inserted into the punctal opening by the use of a combination dilator/inserter tool. Illustrations of operative dilator/inserter tools may be found by reference to Freeman U.S. Pat. No. Des. 295,445. This tool comprises a generally cylindrical body with a relatively pointed dilator tip at one end and a fine cylindrical member at the opposite end which carries an encircling, telescoping sleeve.

When anesthesia is adequate, the punctal zone 64 is grasped between two cotton tip applicator forceps 66 and 68 and rotated slightly to an open posture.

Figure 5C:
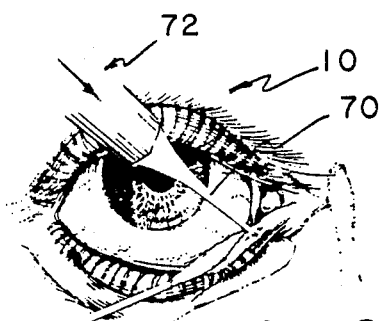

Referring now to FIG. 5C, the punctum is carefully and slowly dilated with the pointed dilator end 70 of the dilator inserter 72. In this procedure the tip may be moistened in a sterile saline solution and slowly projected coaxially into the proximal portion of the canaliculus by a slow twirling motion to facilitate penetration.

Figure 5D:
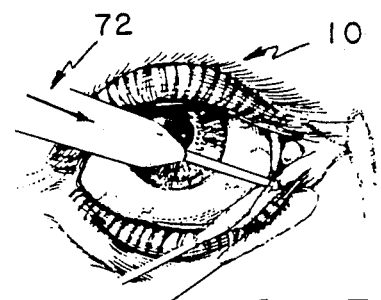
Figure 5E:
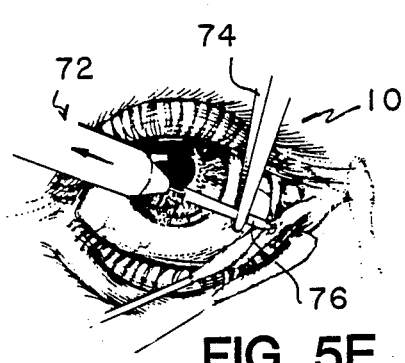

Referring now to FIG. 5D, the dilator inserter tool 72 is turned end for end and a punctum plug, such as illustrative disclosed in FIG. 3 or FIG. 4, positioned upon the cylindrical tip of the inserter by friction engagement of the tip within the cylindrical bore, is inserted into the puncta until the head portion 28 or 46 is seated against the outer punctal surface, note FIG. 2.

Once the lacrimal fluid modulating device is positioned, such as illustrated in FIG. 2, the cap 28 snugly abutting against the punctal opening 24, forceps 74 are used to grasp the outer sleeve 76 of the dilator inserter tool and the tool 72 is then withdrawn. Leaving the lacrimal fluid modulating device in the posture depicted in FIG. 2.

Figure 5F:
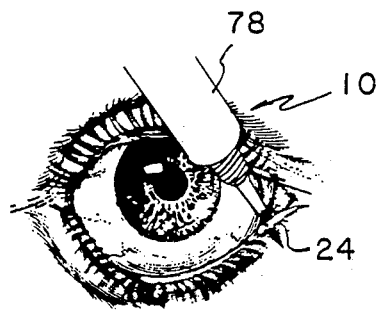

As an optional procedure, a physician may choose to apply topical antibiotic drops as indicated in FIG. 5F through a conventional applicator 78. The drops may be applied directly to the punctal opening area 24 to bathe the inserted lacrimal fluid modulating device with antibiotic solution.

BRIEF SUMMARY OF MAJOR ADVANTAGES OF THE INVENTION

In describing a method and apparatus for efficiently modulating the flow of lacrimal fluid through a puncta and associated canaliculus, in accordance with preferred embodiments of the invention, those skilled in the art will recognize several advantages which singularly distinguish the subject invention from the heretofore known prior art. A particular advantage of the subject invention is the provision of a known diameter bore to drain lacrimal fluid from the eye of a patient. Although the punctal opening and associated canaliculus naturally serves this function, the outflow of lacrimal fluid can be selectively modulated by a physician for an optimum flow for a particular patient.

The axial opening or bore has been shown to provide its desirable features when it is fashioned to be not less than 0.12 mm in diameter and not greater than 0.36 mm with a preferred diameter of 0.24 mm.

The bore may be tapered from the inlet to the outlet in one embodiment and in another embodiment, a stepped bore configuration has been found to facilitate insertion and use with a dilator inserter tool.

A plurality of peripheral members may be positioned at a second, outlet, end of the fluid flow modulating device. This peripheral portion facilitates insertion of the unit through a patient's punctum opening and thereafter cooperates with the internal canaliculus to retain the member in an optimum axial position. Still further the plurality of peripheral members serve to structurally enhance the dimensional integrity of the unit at the outlet end where a relatively small diameter is to be maintained in an open condition.

The lacrimal fluid modulating device is preferably fashioned from a relatively smooth pliable material such as surgical grade silicon and may be facilely inserted and removed without local anesthesia or corrective surgery.

In describing the invention, reference has been made to preferred embodiments. Those skilled in the art, and familiar with the disclosure of the subject invention, may recognize additions, deletions, modifications, substitutions and/or other changes which will fall within the purview of the invention as defined in the following claims.

We claim:

1. A lacrimal fluid modulating device for controlling the flow of the lacrimal fluid through the punctum and associated canaliculus of a human eye comprising:
   a generally cylindrical body member having an axial bore extending from a first, inlet, end of said generally cylindrical body to a second, outlet, end thereof;
   an arcuate head member fashioned at said first end of said generally cylindrical body, said arcuate head member having,
      a bore coaxial with the bore of said generally cylindrical body, and
      the exterior diameter of said arcuate head member being greater than the exterior diameter of said generally cylindrical body member;
   means peripherally fashioned about the exterior surface of said generally cylindrical body member at said second end of said body member, for facilitating placement of said generally cylindrical body member through a punctum of a patient and for retaining said cylindrical body member within an associated canaliculus; and
   said axial bore extending completely through said generally cylindrical body member to operably modulate the flow of lacrimal fluid through the punctum and associated canaliculus and thus enhancing the retention of lacrimal fluid within the eye of a patient.

2. A lacrimal fluid modulating device as defined in claim 1 wherein:
   the internal diameter of said axial bore at said first, inlet, end is greater than the internal diameter of said axial bore at said second, outlet, end.

3. A lacrimal fluid modulating device as defined in claims 1 or 2 wherein:
   the internal diameter of said axial bore of said generally cylindrical body member at said second, outlet, end is not less than 0.12 mm and not greater than 0.36 mm.

4. A lacrimal fluid modulating device as defined in claim 3 wherein:
   the internal diameter of said axial bore of said generally cylindrical body member at said second, outlet, end is substantially equal to 0.24 mm.

5. A lacrimal fluid modulating device as defined in claim 2 wherein: said axial bore is tapered from said first, inlet, end to said second, outlet end.

6. A lacrimal fluid modulating device as defined in claim 2 wherein:
   said axial bore is stepped from a first diameter at said first, inlet, end of said generally cylindrical body to a smaller, second diameter at said second, outlet, end of said generally cylindrical body.

7. A lacrimal fluid modulating device as defined in claim 1 wherein said means peripherally fashioned about the exterior surface of said generally cylindrical body member comprises:
   a single conical exterior surface extending upwardly and outwardly from an initial position at the second, outlet, end of said generally cylindrical body.

8. A lacrimal fluid modulating device as defined in claim 1 wherein said means peripherally fashioned about the exterior surface of said generally cylindrical body member comprises:
   a first conical exterior surface extending upwardly and outwardly from said second, outlet, end of said generally cylindrical body member; and at least a second conical surface extending upwardly and outwardly upstream of said first conical surface from a position upon the exterior surface of said generally cylindrical body member upstream of said second, outlet, end of said generally cylindrical body member.

9. A lacrimal fluid modulating device as defined in claim 8 wherein:

said axial bore is stepped from a first diameter at said first, inlet, end of said generally cylindrical body to a smaller, second, diameter at the second, outlet, end of said generally cylindrical body member.

10. A lacrimal fluid modulating device as defined in claim 9 wherein:

said second diameter of said axial bore of said generally cylindrical body member at said second, outlet, end is not less than 0.12 mm and not greater than 0.36 mm.

11. A method for modulating the flow of lacrimal fluid through the punctum an associated canaliculus of a human eye comprising:

dilating a punctum opening of a patient;

inserting through the dialated punctum opening and partially into an associated canaliculus, a modulating device having a generally cylindrical body, a head portion and an enlarged tip portion, until the head rests upon the punctal opening and the enlarged tip extends into the associated canaliculus to retain the modulating device in place; and maintaining a bore through said modulating device to permit a regulated flow of lacrimal fluid from the eye of a patient through the punctum and associated canaliculus.

12. A method for modulating the flow of lacrimal fluid as defined in claim 11 wherein said step of maintaining a bore comprises:

providing a bore through the generally cylindrical body within an internal diameter at the enlarged tip end not less than 0.12 mm and not greater than 0.36 mm.

* * * * *